United States Patent
Murakoshi

(10) Patent No.: US 10,952,647 B2
(45) Date of Patent: Mar. 23, 2021

(54) SENSOR DEVICE, SENSING METHOD, AND INFORMATION PROCESSING DEVICE

(71) Applicant: SONY CORPORATION, Tokyo (JP)

(72) Inventor: Sho Murakoshi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 630 days.

(21) Appl. No.: 15/543,483

(22) PCT Filed: Dec. 3, 2015

(86) PCT No.: PCT/JP2015/084065
§ 371 (c)(1),
(2) Date: Jul. 13, 2017

(87) PCT Pub. No.: WO2016/136073
PCT Pub. Date: Sep. 1, 2016

(65) Prior Publication Data
US 2018/0008170 A1  Jan. 11, 2018

(30) Foreign Application Priority Data
Feb. 23, 2015  (JP) .............................. JP2015-032466

(51) Int. Cl.
| A61B 5/11 | (2006.01) |
| A63B 69/36 | (2006.01) |
| A63B 24/00 | (2006.01) |
| G06K 9/00 | (2006.01) |
| G09B 19/00 | (2006.01) |

(Continued)

(52) U.S. Cl.
CPC .............. *A61B 5/1126* (2013.01); *A61B 5/11* (2013.01); *A63B 24/0003* (2013.01); *A63B 69/36* (2013.01); *G06K 9/00342* (2013.01); *G09B 19/0038* (2013.01); *H01L 27/146* (2013.01); *H04N 5/355* (2013.01)

(58) Field of Classification Search
CPC ..... A61B 5/1126; A61B 5/11; A63B 24/0003; G06K 9/00342
See application file for complete search history.

(56) References Cited

U.S. PATENT DOCUMENTS

| 7,942,824 | B1 * | 5/2011 | Kayyali | ................. A61B 5/021 600/538 |
| 2006/0161363 | A1 * | 7/2006 | Shibasaki | .......... G01C 19/5607 702/94 |

(Continued)

FOREIGN PATENT DOCUMENTS

| JP | 2004-065803 A | 3/2004 |
| JP | 2004-65803 A | 3/2004 |

(Continued)

OTHER PUBLICATIONS

International Search Report and Written Opinion of PCT Application No. PCT/JP2015/084065, dated Mar. 8, 2016, 01 pages of English Translation and 06 pages of ISRWO.

*Primary Examiner* — Janet L Suglo
(74) *Attorney, Agent, or Firm* — Chip Law Group

(57) ABSTRACT

The sensor device includes a sensor unit that detects information of an object, an attachment portion detachably attached to one or more attachment positions on the object, and an acquisition unit that acquires information indicating the attachment position to which the attachment portion is attached.

19 Claims, 7 Drawing Sheets

(51) Int. Cl.
*H01L 27/146* (2006.01)
*H04N 5/355* (2011.01)

(56) References Cited

U.S. PATENT DOCUMENTS

| 2010/0094103 A1* | 4/2010 | Kaplan | A61B 5/4809 |
| | | | 600/301 |
| 2013/0131465 A1* | 5/2013 | Yamamoto | A61B 5/7271 |
| | | | 600/301 |

FOREIGN PATENT DOCUMENTS

| JP | 2012-200540 A | 10/2012 |
| JP | 2014-183931 A | 10/2014 |

* cited by examiner

SENSOR DEVICE, SENSING METHOD, AND INFORMATION PROCESSING DEVICE

CROSS REFERENCE TO RELATED APPLICATIONS

This application is a U.S. National Phase of International Patent Application No. PCT/JP2015/084065 filed on Dec. 3, 2015, which claims priority benefit of Japanese Patent Application No. JP 2015-032466 filed in the Japan Patent Office on Feb. 23, 2015. Each of the above-referenced applications is hereby incorporated herein by reference in its entirety.

TECHNICAL FIELD

The present disclosure relates to a sensor device, a sensing method, and an information processing device.

BACKGROUND ART

In recent years, attempts have been made to apply information processing technology in various fields. One example is the technique of visualizing the movement of the player's body in the field of sports. It is possible for the player to check whether the action corresponding to the sport is performed smoothly by measuring and recording the movement of his/her body using various sensor devices. This makes it possible for the player to improve easily his/her posture or the like with reference to the visualized body movement.

Techniques for visualizing the body's movement have various approaches including motion capture. In one example, Patent Literature 1 mentioned below discloses a technique of measuring the acceleration by an acceleration sensor mounted on the hand of a player and calculating the speed of the tip of game playing equipment that the player swings on the basis of the measurement result.

CITATION LIST

Patent Literature

Patent Literature 1: JP 2012-200540A

DISCLOSURE OF INVENTION

Technical Problem

However, the technique disclosed in the above-mentioned Patent Literature 1 is intended to measure the acceleration of a specific part in a particular game, so it is difficult to measure the acceleration of a nonspecific part. Furthermore, it is also conceivable that a preferred measuring object or a measuring part varies with change in the type of games, so it is desirable to be able to execute more flexible measurement for visualizing the body's movement. Thus, the present disclosure provides a novel and improved sensor device, sensing method, and information processing device, capable of executing more flexible measurement for visualizing the movement of an object.

Solution to Problem

According to the present disclosure, there is provided a sensor device including: a sensor unit configured to sense information relating to an object; an attachment portion configured to detachably attached to any of one or more attachment positions provided on the object; and an acquisition unit configured to acquire information indicating the attachment position to which the attachment portion is attached.

In addition, according to the present disclosure, there is provided a sensing method that is executed by a sensor device, the sensing method including: sensing information relating to an object; and acquiring information indicating an attachment position to which an attachment portion is attached, the attachment portion being detachably attached to any of one or more attachment positions provided on the object.

In addition, according to the present disclosure, there is provided an information processing device including: an acquisition unit configured to acquire sensor information and information indicating an attachment position to which a sensor device is attached, the sensor information and the information indicating the attachment position being acquired by the sensor device detachably attached to any of one or more the attachment positions provided on an object; and a processing unit configured to process the sensor information acquired by the acquisition unit on the basis of the information indicating the attachment position.

Advantageous Effects of Invention

As described above, according to the present disclosure, it is possible to execute more flexible measurement for visualizing the movement of an object. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
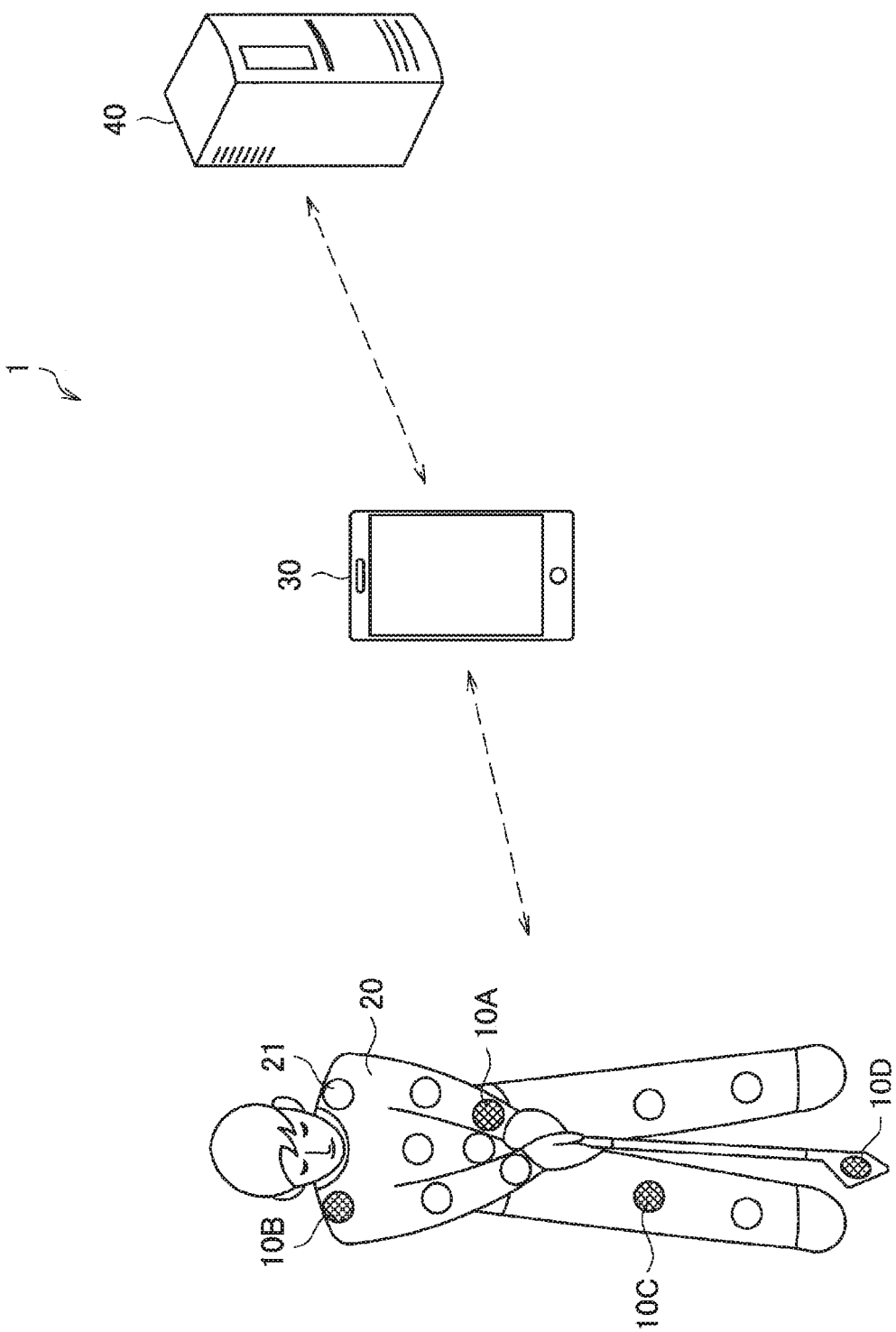
FIG. 1 is a diagram illustrated to describe an overview of a sensing system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated description of these structural elements is omitted.

Further, there is a case in which elements having substantially the same function are discriminated by affixing different alphabets to the back of the same reference numeral in the present specification and drawings. In one example, elements having substantially the same functional configuration are discriminated as sensor devices 10A, 10B, and 10C as necessary. However, when there is no need to discriminate particularly between a plurality of elements having substantially the same functional configuration, only the same reference numeral is affixed. In one example, when there is no need to discriminate particularly between the sensor devices 10A, 10B, and 10C, these sensor devices are referred to collectively as a sensor device 10.

Moreover, the description will be given in the following order.
1. Overview
1.1. General structure
1.2. Technical challenges
2. Configuration example
2.1. Appearance configuration example of sensor device
2.2. Functional configuration example of sensor device
2.3. Functional configuration example of smartphone
2.4. Functional configuration example of server
3. Function details
3.1. Function of acquiring attachment position information
3.2. Sensor setting function
3.3. Information transmission function
3.4. Service providing function
4. Action processing example
5. Hardware configuration example
6. Summary

1. Overview

1.1. General Configuration

An overview of a sensing system according to an embodiment of the present disclosure is described now with reference to FIG. 1.

FIG. 1 is a diagram illustrated to describe an overview of a sensing system 1 according to the present embodiment. As illustrated in FIG. 1, the sensing system 1 includes one or more sensor devices 10 (10A to 10D) that are attached to sensor mounting equipment 20, and includes information processing devices 30 and 40.

The sensor device 10 is a device for sensing various data. The sensor device 10 is attached to a sensor fixture 21 included in the sensor mounting equipment 20 and performs sensing intended for the movement of an object. The object may be a human being, a dog, a cat, or other living things, or an inanimate object such as a robot. In the example illustrated in FIG. 1, the object is a user (human). In addition, the object may be a thing used by a living thing. In one example, the object may be a tool used for games, such as a golf club, a tennis racket, balls, a ski, ski boots, a goal, a bat, or the like. In addition, the object may be a tool for disabled people to manage their daily living, such as prosthesis or wheelchair. In addition, the object may be equipment used for an animal, such as a collar or a horseshoe. The sensor device 10 establishes a wireless connection with the information processing device 30, and so the sensor device 10 transmits the acquired data to the information processing device 30 or receives an instruction from the information processing device 30.

The sensor device 10 is capable of measuring various data by either alone or in combination with another sensor device 10. The sensor device 10 may include, in one example, an inertial sensor such as an acceleration sensor or a gyro sensor. In this case, one sensor device 10 is capable of measuring the inclination of an attachment position. In addition, two sensor devices 10 are capable of measuring the degree of bending of the joint sandwiched between the two sensor devices 10. In addition, a plurality of sensor devices 10 are capable of measuring the time axis order of the maximum value of the angular velocity at each attachment position. Moreover, the processing of calculating the information described above from a sensing result (sensor information) obtained by the sensor device 10 can be performed by, in one example, the information processing devices 30 and 40.

The sensor mounting equipment 20 is a device used to fix the sensor device 10 to an object. As illustrated in FIG. 1, the sensor mounting equipment 20 has one or more attachment positions (sensor fixtures 21) for detachably attaching the sensor device 10, and the sensor device 10 can be attached to any part or the whole of the attachment positions. The sensor mounting equipment 20 may have a shape covering a part or all of the trunk, limbs, or other parts of the user, and in this case, the sensor mounting equipment 20 is preferably formed of a material that can be expanded and contracted so as not to disturb the movement of the user. In addition, the attached sensor device 10 may be located at a distance from the object, and the sensor mounting equipment 20 may be a thick object such as a helmet, a protector, or the like. In addition, the sensor mounting equipment 20 may be attached to an object such as a golf club, a tennis racket, a ski, or the like, or may be integrally formed with the object. The user can attach the sensor device 10 to the sensor fixture 21 located at a part be measured. The user can attach a plurality of sensor devices 10, and their attachment positions are optional, so flexible measurement is achieved.

The information processing devices 30 and 40 are devices that process information output from the sensor device 10. The information processing devices 30 and 40 can be implemented as a smartphone, a tablet terminal, a PC, a server, or the like. In the example illustrated in FIG. 1, the information processing device 30 is a smartphone, and the information processing device 40 is a server. In one example, each of the smartphone 30 and the server 40 visualizes sensor information acquired by the sensor device 10, feeds back the visualized information to the user, or provides various services such as advice or product recommendation for improving the game ability.

1.2. Technical Challenges

In this regard, humans generally have more than 200 bones. Thus, in order to measure the movement of the whole body at once, the sensor device 10 may be necessary to be attached to 17 body parts in rough estimate. However, it is conceivable that measurement for so many parts is not necessary to check one action such as a golf swing. In addition, in some cases, the characteristic of wireless communication limits the number of sensor devices 10 that can perform simultaneous sensing. In one example, the use of one Bluetooth (registered trademark) dongle allows up to seven child devices to communicate, so the upper limit of the sensor device 10 that can perform simultaneous sensing is seven.

In view of the above circumstances, it is conceivable in practice that the user performs measurement while changing the attachment position of the sensor device 10. In this case, a large number of sensor devices 10 do not necessarily have to used, so it is cost-effective. Considering that the user performs measurement while changing the attachment position of the sensor device 10, it is desirable from the viewpoint of convenience of the user that the sensing system 1 can automatically know the attachment position of the sensor device 10.

Thus, in view of the above circumstances, the sensing system 1 according to an embodiment of the present disclosure is developed. The sensor device 10 according to the present embodiment can automatically know its own attachment position. The sensing system 1 according to the present embodiment will be described in detail with reference to FIGS. 2 to 8.

2. Configuration Example

A configuration example of each component included in the sensing system 1 according to the present embodiment is described below one by one with reference to FIGS. 2 to 5.

2.1. Appearance Configuration Example of Sensor Device

Figure 2:
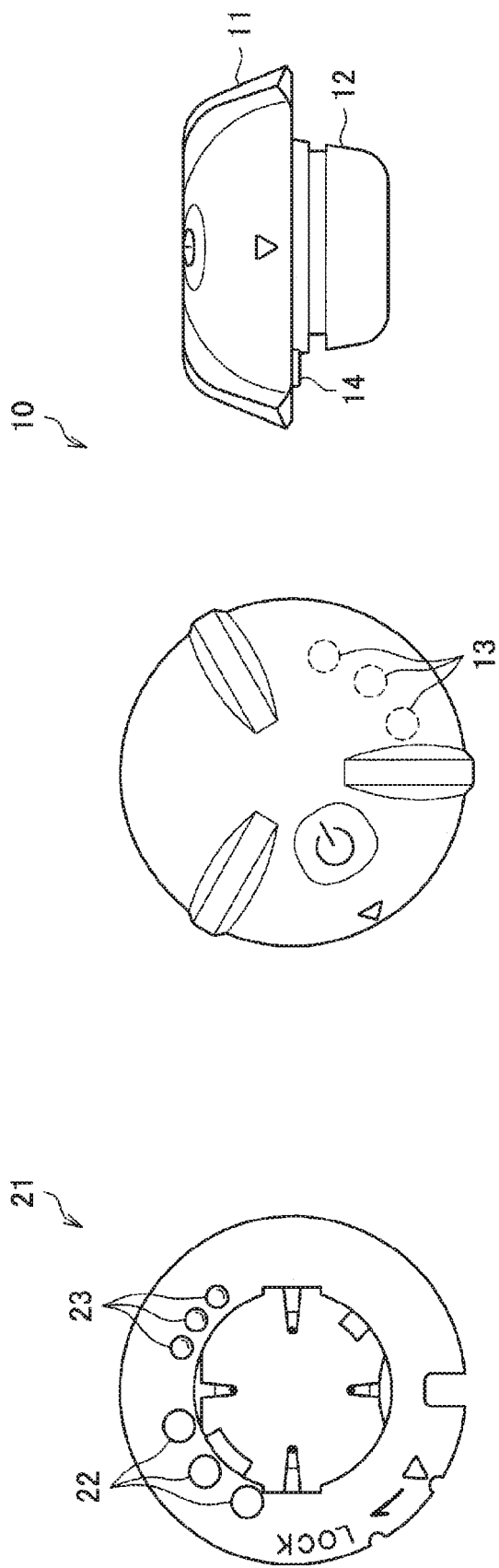
FIG. 2 is a diagram illustrated to describe an example of an appearance configuration of a sensor device and a sensor fixture according to the present embodiment.

FIG. 2 is a diagram illustrated to describe an example of an appearance configuration of the sensor device 10 and the sensor fixture 21 according to the present embodiment. As illustrated in FIG. 2, the sensor device 10 includes a main body portion 11 and an attachment portion 12. The main body portion 11 includes, in one example, a sensor. The attachment portion 12 is detachably attached to one of one or more sensor fixtures 21 provided on the user (on the sensor mounting equipment 20). In one example, the attachment portion 12 has a groove formed along the surface of the cylinder and is threadedly engaged with the sensor fixture 21.

The sensor device 10 is provided with a terminal 13. The sensor fixture 21 is also provided with a terminal 22. In one example, when the sensor device 10 is attached to the sensor fixture 21, the terminal 13 and the terminal 22 are in contact with each other, and electric signals can be exchanged.

The sensor device 10 is provided with a switch 14. The sensor fixture 21 is provided with a concavo-convex portion 23. In one example, when the sensor device 10 is threadedly engaged with the sensor fixture 21, the convex portions of the concavo-convex portions 23 sequentially press the switches 14. In the example illustrated in FIG. 2, when the sensor device 10 is threadedly engaged with the sensor fixture 21, three convex portions of the concavo-convex portions 23 are aligned in a row at equal intervals in an arc shape along the trajectory of the switch 14 so that the convex portions sequentially press the switches 14. However, the present technology is not limited to this example. In one example, the number of convex portions may be optional, formed at optional intervals, or formed in a plurality of rows. In a case where the convex portions are provided in a plurality of rows, it is preferable that the switches 14 are also provided in a plurality of rows.

2.2. Functional Configuration Example of Sensor Device

Figure 3:
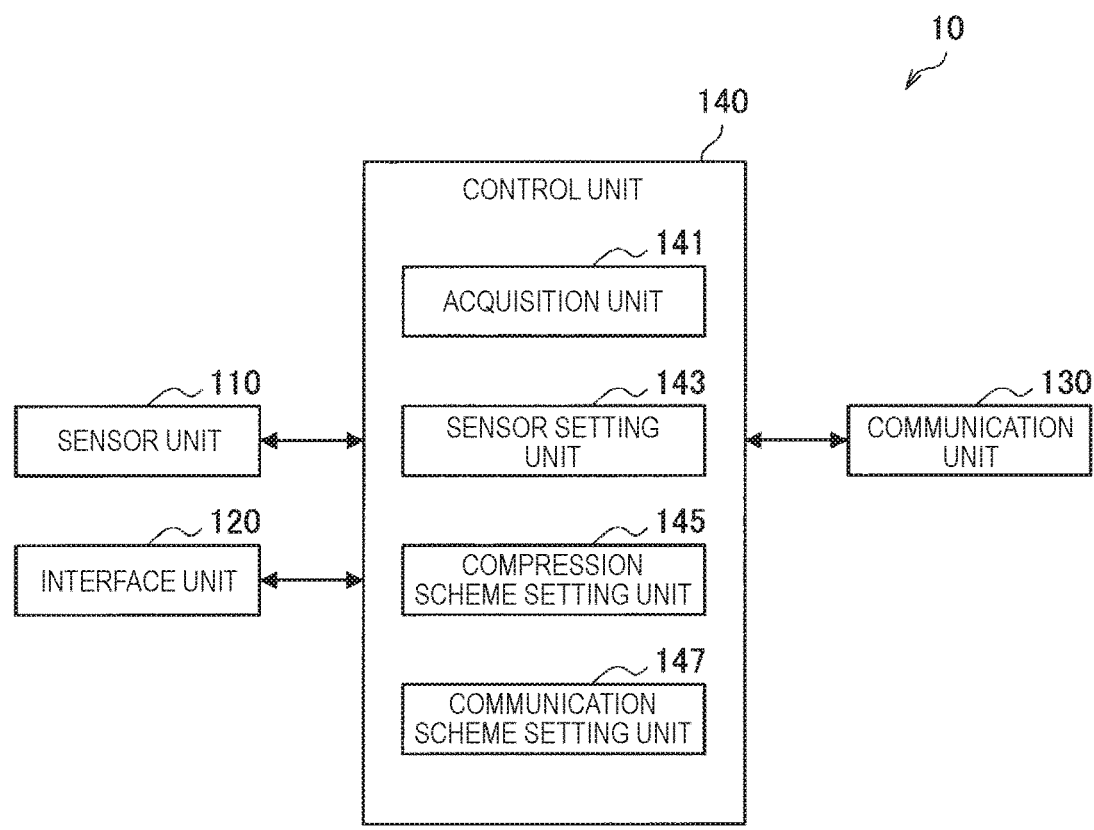
FIG. 3 is a block diagram illustrating an example of a logical configuration of a sensor device according to the present embodiment.

FIG. 3 is a block diagram illustrating an example of a logical configuration of the sensor device 10 according to the present embodiment. As illustrated in FIG. 3, the sensor device 10 is configured to include a sensor unit 110, an interface unit 120, a communication unit 130, and a control unit 140.

The sensor unit 110 has a function of sensing information relating to an object. In one example, the sensor unit 110 is implemented as an inertia sensor such as an acceleration sensor and a gyro sensor. In addition, the sensor unit 110 may include a biological information measuring unit such as a myoelectric sensor, a neural sensor, a pulse sensor, and a body temperature sensor. In addition, the sensor unit 110 may include a vibration sensor, a geomagnetic sensor, or the like. The sensor unit 110 outputs the sensor information to the control unit 140.

The interface unit 120 is an interface with the sensor fixture 21 to which the sensor device 10 is attached. In one example, the interface unit 120 includes the terminal 13 and the switch 14. In one example, the interface unit 120 outputs information, which relates to the electric signal flowing between the terminal 13 and the terminal 22, to the control unit 140. In addition, the interface unit 120 outputs information, which relates to the depression of the switch 14 by the concavo-convex portion 23, to the control unit 140.

The communication unit 130 is a communication module that transmits and receives data to and from an external device. In one example, the communication unit 130 transmits and receives data to and from the smartphone 30. The communication unit 130 directly communicates with the smartphone 30 using a communication scheme such as a wireless local area network (LAN), Wireless Fidelity (Wi-Fi, registered trademark), infrared communication, and Bluetooth, or indirectly communicates with the smartphone 30 via another communication node such as a network access point. The communication unit 130 may perform wired communication with an external device using a communication scheme such as a wired LAN.

The control unit 140 functions as an arithmetic processing unit and a control unit, and controls the overall operation in the sensor device 10 in accordance with various programs. As illustrated in FIG. 3, the control unit 140 functions as an acquisition unit 141, a sensor setting unit 143, a compression scheme setting unit 145, and a communication scheme setting unit 147. The acquisition unit 141 has a function of acquiring information indicating the attachment position (sensor fixture 21) to which the attachment portion 12 is attached. The information indicating the attachment position is hereinafter also referred to as attachment position information. The sensor setting unit 143 has a function of configuring settings for the sensor unit 110. The compression scheme setting unit 145 has a function of setting a compression scheme of data to be transmitted to an external device by the communication unit 130. The communication scheme setting unit 147 has a function of setting a communication scheme to be used in transmitting data to an external device by the communication unit 130.

2.3. Function Configuration Example of Smartphone

Figure 4:
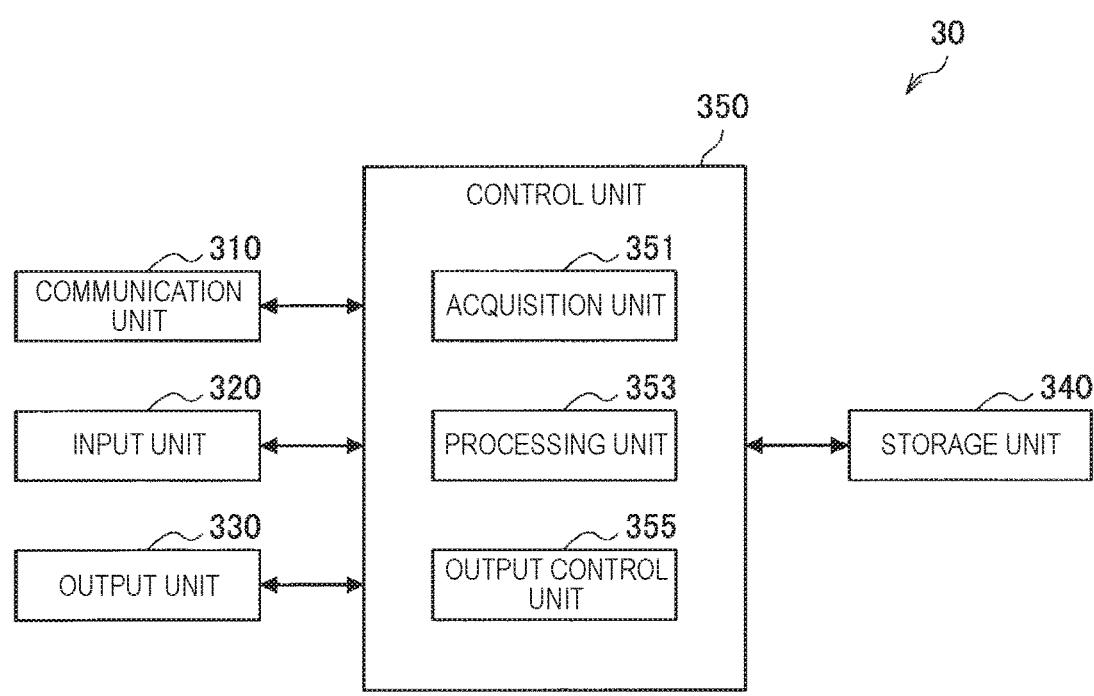
FIG. 4 is a block diagram illustrating an example of a logical configuration of a smartphone according to the present embodiment.

FIG. 4 is a block diagram illustrating an example of a logical configuration of the smartphone 30 according to the present embodiment. As illustrated in FIG. 4, the smartphone 30 is configured to include a communication unit 310, an input unit 320, an output unit 330, a storage unit 340, and a control unit 350.

The communication unit 310 is a communication module that transmits and receives data to and from an external device. In one example, the communication unit 310 transmits and receives data to and from the sensor device 10 and the server 40. The communication unit 310 directly communicates with the sensor device 10 or the server 40 using a communication scheme such as a wireless LAN, Wi-Fi, infrared communication, Bluetooth, and wired LAN, or indirectly communicates with the sensor device 10 or the server 40 via another communication node such as a network access point.

The input unit 320 has a function of receiving an operation by a user. In one example, the input unit 320 is implemented as a keyboard, a mouse, or the like. In addition, the input unit 320 may be implemented as a touch panel integrally formed with a display device (the output unit 330).

The output unit 330 has a function of outputting information to the user in the form of video, image, audio, or the like. The output unit 330 is implemented as, in one example, a cathode ray tube (CRT) display device, a liquid crystal display device, a loudspeaker, or the like.

The storage unit 340 is a unit that records data on and reproduces data from a predetermined recording medium. In one example, the storage unit 340 stores data received from the sensor device 10 through the communication unit 310.

The control unit 350 functions as an arithmetic processing unit and a control unit, and controls the overall operation in the smartphone 30 in accordance with various programs. As illustrated in FIG. 4, the control unit 350 functions as an acquisition unit 351, a processing unit 353, and an output control unit 355. The acquisition unit 351 has a function of acquiring sensor information and attachment position information acquired by the sensor device 10 through the communication unit 310. The processing unit 353 has a function of processing the sensor information acquired by the acquisition unit 351 on the basis of the attachment position information. The output control unit 355 has a function of controlling the output unit 330 so that the output unit 330 outputs information.

2.4. Functional Configuration Example of Server

Figure 5:
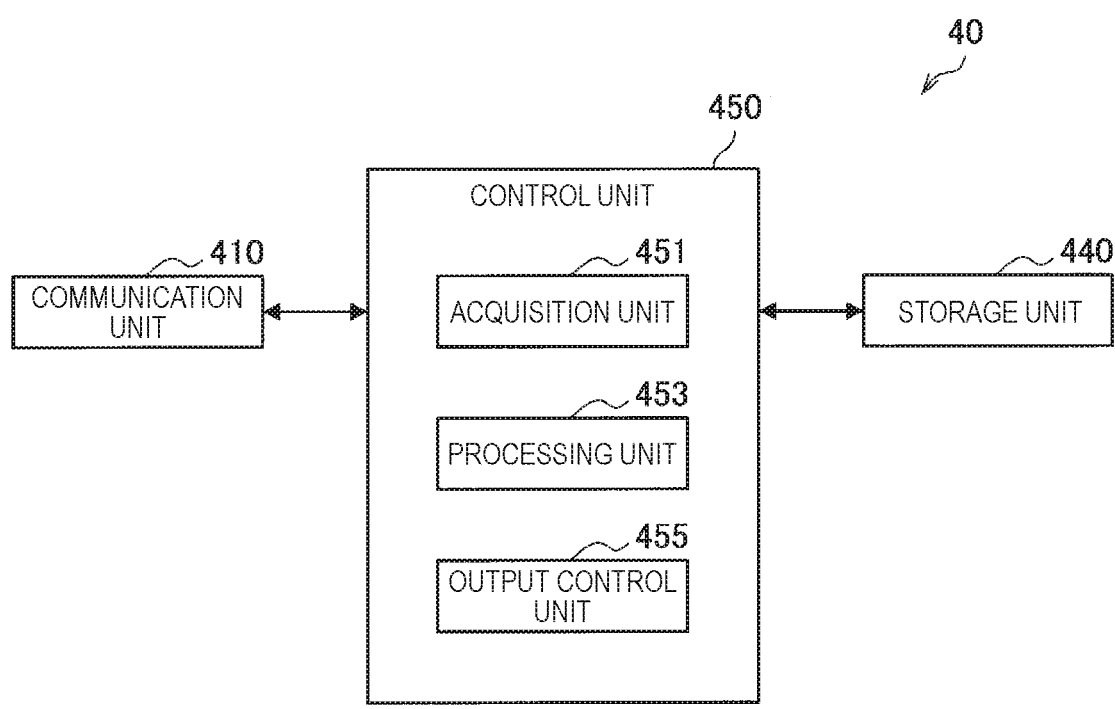
FIG. 5 is a block diagram illustrating an example of a logical configuration of a server according to the present embodiment.

FIG. 5 is a block diagram illustrating an example of a logical configuration of the server 40 according to the present embodiment. As illustrated in FIG. 5, the server 40 is configured to include a communication unit 410, a storage unit 440, and a control unit 450.

The communication unit 410 is a communication module that transmits and receives data to and from an external device. In one example, the communication unit 410 transmits and receives data to and from the smartphone 30. The communication unit 410 directly communicates with the smartphone 30 using a communication scheme such as a wireless LAN, Wi-Fi, infrared communication, Bluetooth, and wired LAN, or indirectly communicates with the smartphone 30 via another communication node such as a network access point.

The storage unit 440 is a unit that records data on and reproduces data from a predetermined recording medium. In one example, the storage unit 440 stores data received from the smartphone 30 through the communication unit 410.

The control unit 450 functions as an arithmetic processing unit and a control unit, and controls the overall operation in the server 40 in accordance with various programs. As illustrated in FIG. 5, the control unit 450 functions as an acquisition unit 451, a processing unit 453, and an output control unit 455. The acquisition unit 451 has a function of acquiring sensor information and attachment position information acquired by the sensor device 10 via the communication unit 410. The processing unit 453 has a function of processing the sensor information acquired by the acquisition unit 451 on the basis of the attachment position information. The output control unit 455 has a function of controlling information output by the output unit 330 of the smartphone 30.

The configuration example of each component included in the sensing system 1 according to the present embodiment is described above. Subsequently, functions of the sensing system 1 according to the present embodiment are described in detail.

3. Function Details

3.1. Function of Acquiring Attachment Position Information

In a case where the sensor device 10 (e.g., the acquisition unit 141) is attached to the sensor fixture 21, the sensor device 10 acquires the attachment position information. The attachment position information may be information indicating a particular part such as wrist, shoulder, or chest of the user. In addition, the attachment position information may be identification information of the sensor fixture 21, and if the position and identification information of each of the sensor fixtures 21 in the sensor mounting equipment 20 are known, the sensing system 1 can specify each particular position.

In one example, the acquisition unit 141 may acquire the attachment position information on the basis of electrical characteristics of the sensor fixture 21 to which the attachment portion 12 is attached. In one example, the acquisition unit 141 acquires a resistance value obtained by passing an electric current between the terminal 13 and the terminal 22, which are in contact with each other, as the attachment position information. The sensing system 1 may specify the sensor fixture 21 to which the attachment portion 12 is attached from the resistance value acquired by the acquisition unit 141.

In one example, the acquisition unit 141 may acquire the attachment position information on the basis of a physical shape of the sensor fixture 21 to which the attachment portion 12 is attached. In one example, when the sensor device 10 is threadedly engaged with the sensor fixture 21, the acquisition unit 141 acquires a concavo-convex pattern (e.g., the number and interval of the convex portions, and the height of the convex portion) of the concavo-convex portion 23. The concavo-convex pattern is obtained by causing the concavo-convex portion 23 to press the switch 14 as the attachment position information. The sensing system 1 may specify the sensor fixture 21 to which the attachment portion 12 is attached from the concavo-convex pattern acquired by the acquisition unit 141.

Any of the approaches allows the sensing system 1 to acquire automatically the attachment position information by attaching the sensor device 10 to the sensor fixture 21. In one example, this prevents the user from entering the attachment position information, thereby improving the user's convenience.

The acquisition unit 141 is capable of acquiring various types of information using the above-described mechanism.

In one example, settings for identification of individuals in a team may be performed for the terminal 22 and/or the concavo-convex portion 23 of the sensor fixture 21. In this case, the acquisition unit 141 may acquire information, which indicates a team of the user to which the attachment is made, a position (e.g., offense or defense) in a game of the user to which the attachment is made, or a uniform number of the user, from the resistance value and/or the concavo-convex pattern.

In addition, in one example, the acquisition unit 141 may acquire information indicating that the attachment is not made. In addition, the acquisition unit 141 may acquire information indicating an object to which the attachment is made. In one example, the acquisition unit 141 may acquire information indicating that the attachment is made to the user, a tool such as golf club, a charger, a device for calibrating the sensor device 10, a shipping inspection machine in a factory, or the like.

3.2. Sensor Setting Function

The sensor device 10 (e.g., the sensor setting unit 143) configures settings of the sensor unit 110 on the basis of the attachment position information acquired by the acquisition unit 141. This makes it possible for the sensing system 1 to acquire the sensor information obtained by performing sensing by using the settings corresponding to characteristics of the sensor information for each attachment position. The sensor setting function corresponding to the characteristics of the sensor information for each attachment position is described below with reference to FIG. 6.

Figure 6:
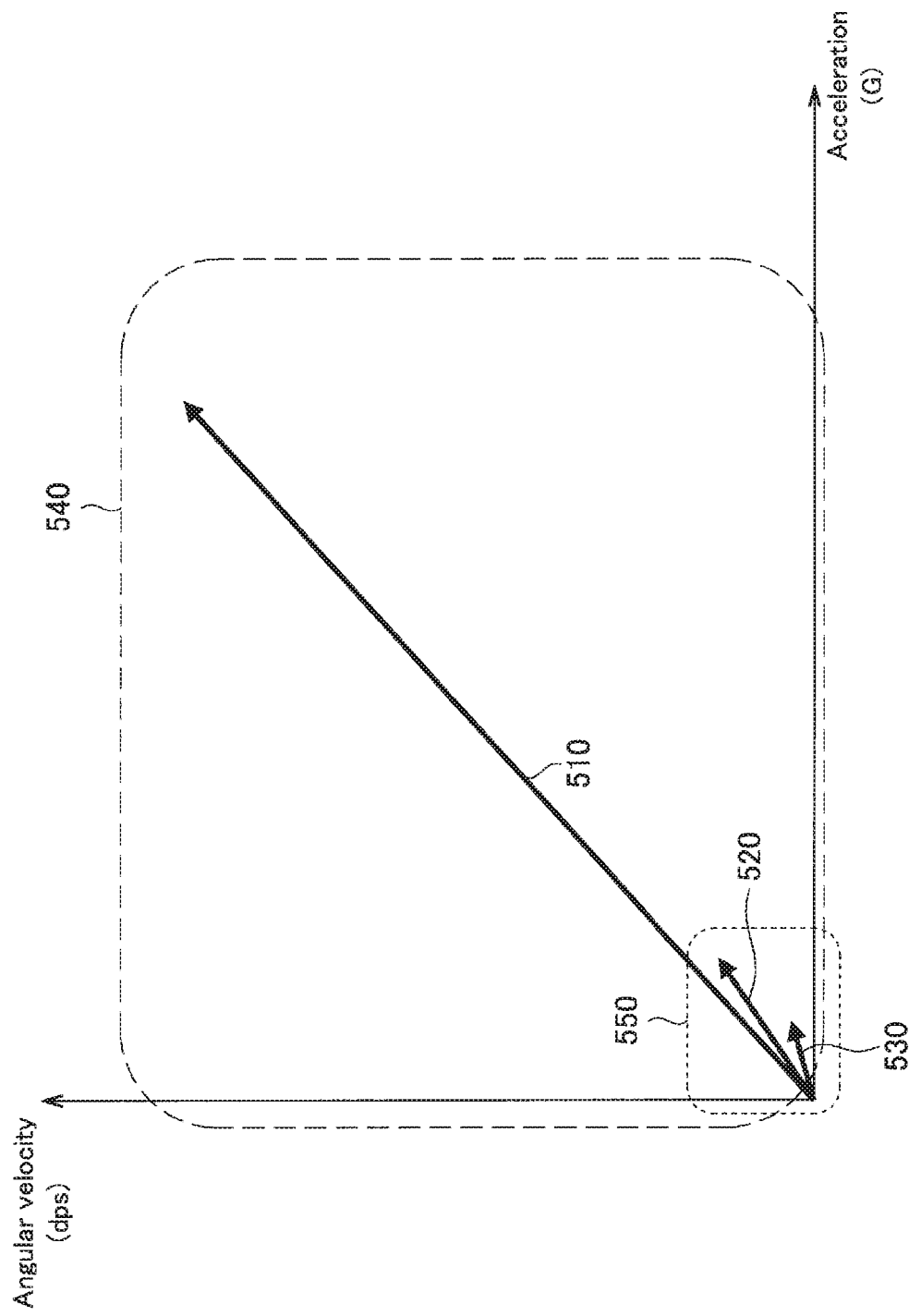
FIG. 6 is a diagram illustrating an example of characteristics of sensor information at each attachment position in golf.

FIG. 6 is a diagram illustrating an example of the characteristics of sensor information for each attachment position in golf. In FIG. 6, the vertical axis represents angular velocity, and the horizontal axis represents acceleration. FIG. 6 illustrates sensor information for each attachment position in golf swing motion. Reference numeral 510 denotes sensor information acquired by the sensor device 10 attached to the back of the hand. Reference numeral 520 denotes sensor information acquired by the sensor device 10 attached to the shoulder. Reference numeral 530 denotes sensor information acquired by the sensor device 10 attached to the waist. As indicated by the reference numeral 510, the sensor device 10 attached to a position far from the body trunk, for example, the back of the hand or the wrist, is preferable to be able to measure up to high angular velocity and acceleration. In addition, as indicated by the reference numeral 520, the sensor device 10 attached to a position close to the body trunk, for example, a waist, a shoulder, a back, or the like, is preferable to be able to measure the angular velocity and the acceleration with high resolution. In addition, in the sensor device 10 attached to an object that generates vibration, such as a hitting tool including a bat and a golf club or a hand holding the hitting tool, it is preferable to be able to perform measurement by using a vibration sensor.

Thus, the sensor setting unit 143 may set at least one of the execution or stop of sensing by the sensor unit 110, dynamic range, and resolution (sampling frequency). In one example, there may be a case where the attachment position of the sensor device 10 is the hitting tool or the back of the hand close to the hitting tool. In this case, the sensor setting unit 143 turns on the vibration sensor to execute sensing, and then may set the dynamic range of the inertial sensor to be wide and the resolution to be low. In the example illustrated in FIG. 6, the sensor setting unit 143 may set the dynamic range to a range indicated by reference numeral 540. This makes it possible for the sensing system 1 to analyze the vibration information and to analyze the angular velocity and the acceleration on condition that the dynamic range is wide. On the other hand, there may be a case where the attachment position of the sensor device 10 is a waist or back close to the body trunk. In this case, the sensor setting unit 143 turns off the vibration sensor to stop the sensing, and then may set the dynamic range of the inertial sensor to be narrow and the resolution to be high. In the example illustrated in FIG. 6, the sensor setting unit 143 may set the dynamic range to a range indicated by reference numeral 550. This makes it possible for the sensing system 1 to prevent unnecessary vibration information from being analyzed, and to analyze the angular velocity and acceleration on condition that the dynamic range is narrow.

The sensor setting unit 143 may configure settings on the basis of at least one of an object or the action performed by the object. In one example, the sensor setting unit 143 may configure different settings depending on whether the object is a user or a tool used by the user. This is because, in some cases, the acceleration and the angular velocity have different minimum values and maximum values depending on whether the sensor device 10 is attached to a user or a tool even when the same action is performed. In addition, the sensor setting unit 143 configures different settings depending on whether the action performed by the object is golf or baseball, or depending on whether the action is a hitting action or a pitching action if the action is baseball. This is because, in some cases, the acceleration and the angular velocity have different minimum values and maximum values depending on the type of action.

The sensor setting unit 143 may recognize the action performed by the object on the basis of a user instruction. In one example, the sensor setting unit 143 may recognize information indicating a game and an action performed by the user on the basis of the user instruction via the smartphone 30. This makes it possible for the sensor setting unit 143 to configure settings corresponding to the above-described action.

In addition, the sensor setting unit 143 may estimate the action performed by the object on the basis of the sensor information sensed by the sensor unit 110 and the attachment position information acquired by the acquisition unit 141. In one example, the sensor setting unit 143 of the sensor device 10 attached to the back of the hand may estimate whether the action performed by the user is a hitting action or a pitching action in baseball on the basis of the presence or absence of vibration, acceleration, and the magnitude of angular velocity. This makes it possible for the sensor setting unit 143 to configure settings corresponding to the above-described action.

Moreover, the information indicating the object may be included in the attachment position information acquired by the acquisition unit 141. The sensor setting unit 143 may certainly acquire the information indicating the object on the basis of the user instruction or on the basis of the sensor information and the attachment position information.

3.3. Information Transmission Function

The sensor device 10 (e.g., the communication unit 130) transmits the sensor information sensed by the sensor unit 110 and the attachment position information acquired by the acquisition unit 141 to the other devices (e.g., the smartphone 30). This makes it possible for the smartphone 30 and the server 40 to acquire the sensor information associated with the attachment position information from each of the sensor devices 10.

The power ON or OFF, the dynamic range, the sampling frequency, or the like of various sensors can vary depending on the attachment position of the sensor device 10, so the amount of data transmitted from the sensor device 10 can change dynamically.

Thus, the compression scheme setting unit 145 may set the compression scheme of the data transmitted by the communication unit 130 depending on setting contents established by the sensor setting unit 143. In one example, there may be a case of setting the contents in which many sensors are powered on, i.e., the amount of information of the sensor information is set to be large, such as high sampling frequency or large number of quantization bits. In this case, the compression scheme setting unit 145 may set a compression scheme having a higher compression ratio to be used. On the other hand, there may be a case of setting the contents in which many sensors are powered off, i.e., the amount of information of the sensor information is set to be small, such as low sampling frequency or small number of quantization bits. In this case, the compression scheme setting unit 145 may set a compression scheme having a lower compression ratio to be used. The setting of the compression scheme may be performed by selecting a compression algorithm, or may be performed by selecting whether to send raw data or processed data. In one example, the communication unit 130 may compress posture information estimated from the angular velocity data using a smaller sampling frequency and then transmit the posture information, rather than transmitting the angular velocity data, without any modification. In this manner, the compression scheme setting unit 145 can adjust the amount of data transmitted depending on the attachment position of the sensor device 10.

Further, the communication scheme setting unit 147 may set the communication scheme used by the communication unit 130 depending on the setting contents established by the sensor setting unit 143. In one example, in the case of the setting contents in which the amount of information of the sensor information is set to be large, the communication scheme setting unit 147 may perform the settings to use the communication scheme with a wide bandwidth such as Classic Bluetooth. On the other hand, in the case of the setting contents in which the amount of information of the sensor information is set to be small, the communication scheme setting unit 147 may perform settings to use a communication scheme with a narrow bandwidth such as Bluetooth LE. In this manner, the communication scheme setting unit 147 can employ a suitable communication scheme corresponding to the attachment position of the sensor device 10.

3.4. Service Providing Function

The sensing system 1 (e.g., the smartphone 30 and/or the server 40) may provide various services using information acquired by the sensor device 10. In one example, the sensing system 1 provides services suitable for the user by analyzing the sensor information and the attachment position information.

In one example, the smartphone 30 may transmit information to the server 40 via the smartphone 30, and may display advice, which is generated by the algorithm inside the server 40, for supporting the improvement as compared to other users. In addition, the smartphone 30 may accumulate information acquired previously to display a change in the skill of the individual user or to recommend a product corresponding to the improvement. In addition, the smartphone 30 may analyze the information received from the sensor device 10 to perform feedback such as display of information in real time, emission of sound, and movement of an actuator provided in another device. The real-time feedback is effective for improvement of the posture, the instruction of the position to be attached, or the like. In addition, the smartphone 30 may store information relating to the swing action with a good posture obtained in accordance with the instruction by a coach of the user, and may feedback the reproduction of the good posture upon acquisition of similar information during personal practice.

The functions of the sensing system 1 according to the present embodiment are described in detail above. Subsequently, an example of operation processing of the sensor device 10 according to the present embodiment is described with reference to FIG. 7.

4. Operation Processing Example

Figure 7:
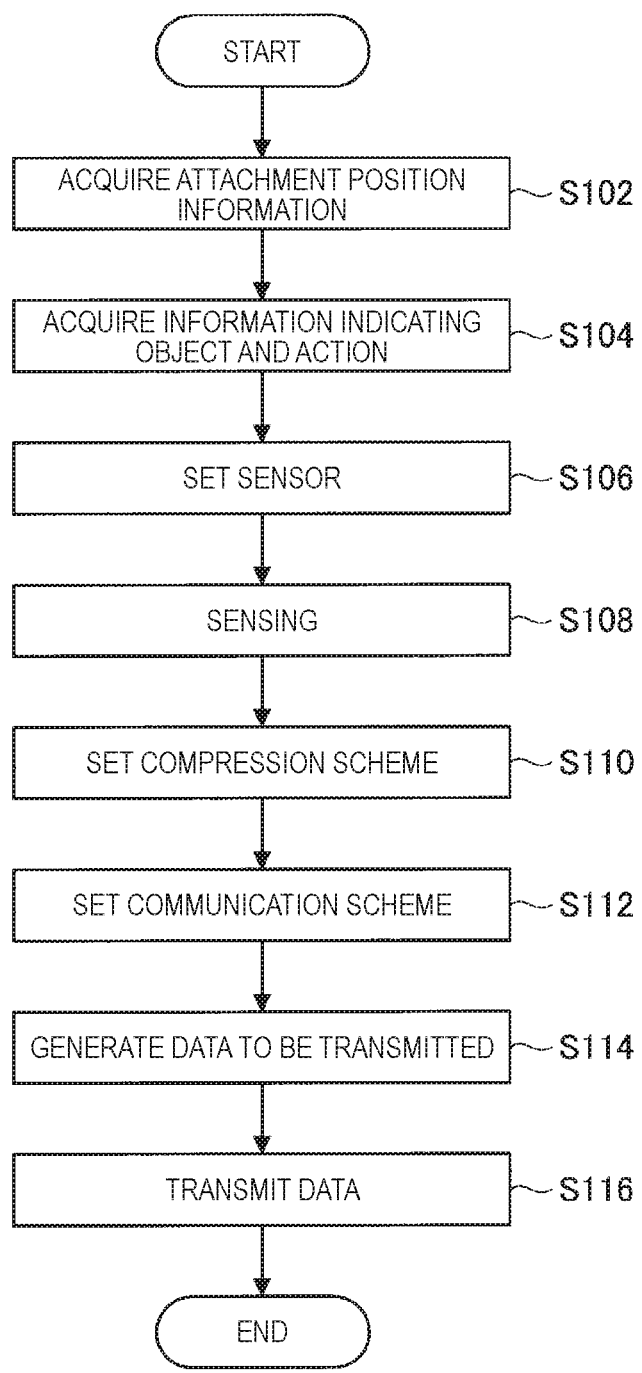
FIG. 7 is a flowchart illustrating an example of the procedure for a sensing process executed in the sensor device according to the embodiment.

FIG. 7 is a flowchart illustrating an example of the procedure for a sensing process executed in the sensor device 10 according to the present embodiment.

As illustrated in FIG. 7, the acquisition unit 141 acquires attachment position information (step S102). Next, the sensor setting unit 143 acquires information indicating an object and information indicating an action performed by the object (step S104). Next, the sensor setting unit 143 configures settings for the sensor unit 110 on the basis of the attachment position information, the object, and the information indicating the action performed by the object (step S106).

Then, the sensor unit 110 performs various sensing processes in accordance with the settings performed by the sensor setting unit 143 (step S108). Next, the compression scheme setting unit 145 sets a compression scheme for data to be transmitted depending on the attachment position information (step S110). In addition, the communication scheme setting unit 147 sets the communication scheme depending on the attachment position information (step S112). Next, the communication unit 130 generates data to be transmitted, which includes the attachment position information and/or the sensor information using the compression scheme that is set by the compression scheme setting unit 145 (step S114). Then, the communication unit 130 transmits the data to be transmitted using the communication scheme that is set by the communication scheme setting unit 147 (step S116).

5. Hardware Configuration Example

Figure 8:
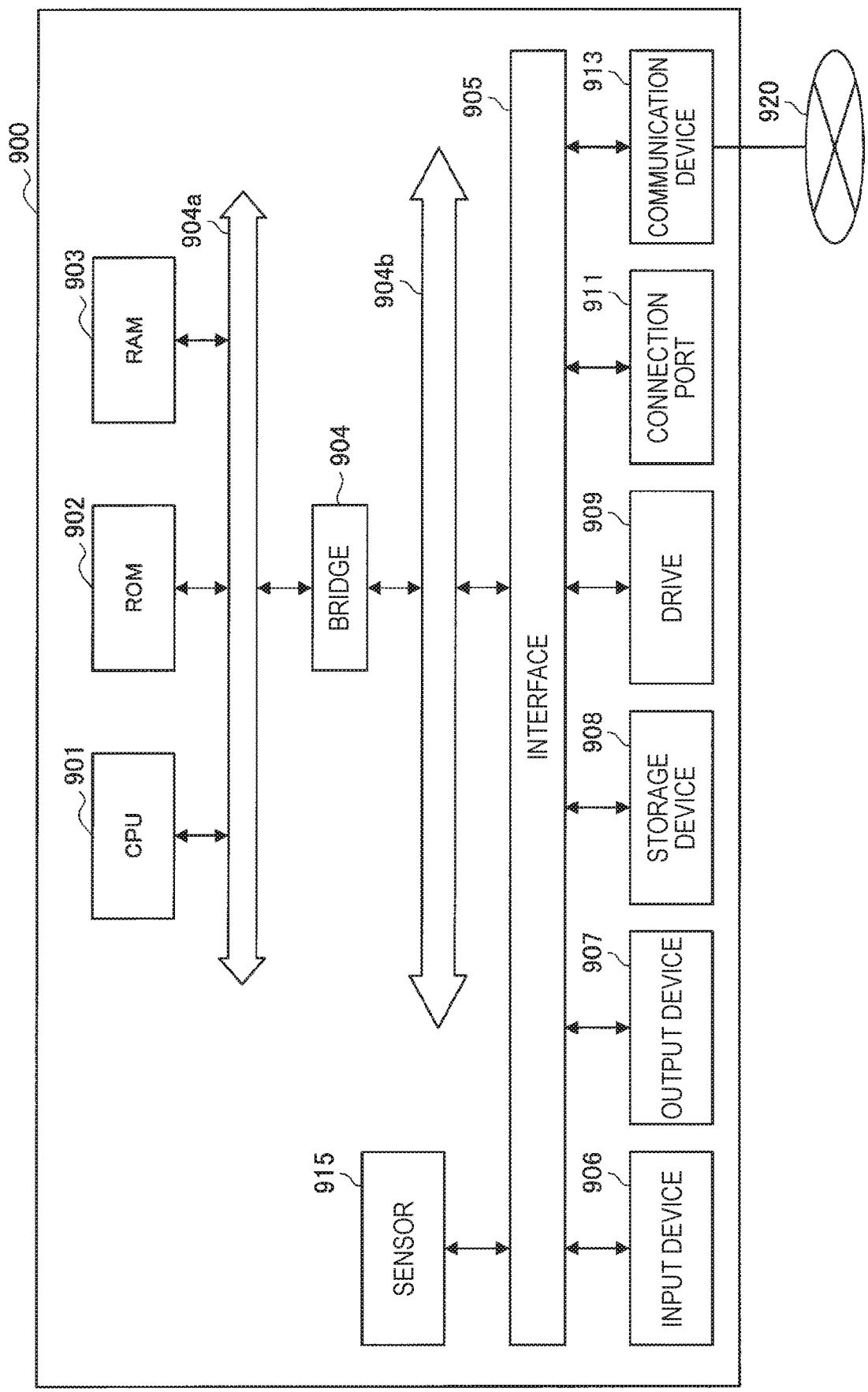
FIG. 8 is a block diagram illustrating an example of a hardware configuration of an information processing device according to the present embodiment.

Finally, a hardware configuration of an information processing device according to the present embodiment will be described with reference to FIG. 8. FIG. 8 is a block diagram illustrating an example of the hardware configuration of the information processing device according to the present embodiment. Moreover, the information processing device 900 illustrated in FIG. 8 may be implemented, in one example, as the sensor device 10, the smartphone 30, and the server 40 illustrated in FIGS. 3 to 5, respectively. The information processing performed by the sensor device 10, the smartphone 30, or the server 40 according to the present embodiment is achieved by cooperation of software and hardware described below.

As illustrated in FIG. 8, the information processing device 900 is configured to include a central processing unit (CPU) 901, a read only memory (ROM) 902, a random access memory (RAM) 903, and a host bus 904*a*. In addition, the information processing device 900 is configured to include a bridge 904, an external bus 904*b*, an interface 905, an input device 906, an output device 907, a storage device 908, a drive 909, a connection port 911, a communication device 913, and a sensor 915. The information processing device 900 may be configured to include a processing circuit such as a DSP or an ASIC instead of or in addition to the CPU 901.

The CPU 901 functions as an arithmetic processing unit and a control unit and controls the overall operation in the information processing device 900 in accordance with various programs. Further, the CPU 901 may be a microprocessor. The ROM 902 stores, for example, an operation parameter and a program used by the CPU 901. The RAM 903 temporarily stores, for example, a program used during execution of the CPU 901 and a parameter appropriately changed in the execution. The CPU 901 may be configured as, in one example, the control unit 140 illustrated in FIG. 3, the control unit 350 illustrated in FIG. 4, and the control unit 450 illustrated in FIG. 5.

The CPU 901, the ROM 902, and the RAM 903 are connected to each other through the host bus 904a including a CPU bus and the like. The host bus 904a is connected, via the bridge 904, to the external bus 904b, an example of which being a peripheral component interconnect/interface (PCI) bus. Moreover, the host bus 904a, the bridge 904, and the external bus 904b are not necessarily configured as a separate component, but their functions may be incorporated into in a single bus.

The input device 906 is implemented as a device allowing the user to input information, such as a mouse, a keyboard, a touch panel, a button, a microphone, a switch, and a lever. In addition, the input device 906 may be a remote controller using infrared ray or other electric waves, or may be externally connected equipment, such as a cellular phone or a PDA, operable in response to the user operation of the information processing device 900. Furthermore, the input device 906 may include an input control circuit or the like which is configured to generate an input signal on the basis of information input by the user using the aforementioned input means and to output the generated input signal to the CPU 901. The user of the information processing device 900 may input various types of data to the information processing device 900, or may instruct the information processing device 900 to perform a processing operation, by the user operation of the input device 906. The input device 906 may be configured as, in one example, the input unit 320 illustrated in FIG. 4.

The output device 907 is configured as a device capable of performing visual or auditory notification of the acquired information to the user. An example of such device includes a display device such as CRT display devices, liquid crystal display devices, plasma display devices, EL display devices, and lamps, a sound output device such as loudspeakers and headphones, and a printer device. The output device 907 outputs, for example, results acquired by various processes performed by the information processing device 900. Specifically, the display device visually displays results acquired by various processes performed by the information processing device 900 in various formats such as text, images, tables, and graphs. On the other hand, the sound output device converts audio signals composed of reproduced sound data, audio data, and the like into analog signals and audibly outputs the analog signals. The aforementioned display device and sound output device may be configured as, for example, the output unit 330 illustrated in FIG. 4.

The storage device 908 is a device for data storage configured as an example of a storage unit of the information processing device 900. In one example, the storage device 908 is implemented as a magnetic storage device such as an HDD, a semiconductor storage device, an optical storage device, a magneto-optical storage device, or the like. The storage device 908 may include a storage medium, a recording device for recording data on the storage medium, a reading device for reading data from the storage medium, a deletion device for deleting data recorded on the storage medium, and the like. The storage device 908 stores programs and various types of data executed by the CPU 901, various types of data acquired from the outside, and the like. The storage device 908 may be configured as, for example, the storage unit 340 illustrated in FIG. 4 or the storage unit 440 illustrated in FIG. 5.

The drive 909 is a reader-writer for storage media and is included in or externally attached to the information processing device 900. The drive 909 reads the information recorded on a removable storage medium such as a magnetic disc, an optical disc, a magneto-optical disc, or a semiconductor memory mounted thereon and outputs the information to the RAM 903. In addition, the drive 909 can write information on the removable storage medium.

The connection port 911 is an interface connected with external equipment and, for example, is a connection port with the external equipment that can transmit data through a universal serial bus (USB) and the like. The connection port 911 may be configured as, for example, the interface unit 120 illustrated in FIG. 3.

The communication device 913 is, for example, a communication interface configured as a communication device or the like for connection with a network 920. The communication device 913 is, for example, a communication card or the like for a wired or wireless local area network (LAN), long term evolution (LTE), Bluetooth (registered trademark), or wireless USB (WUSB). In addition, the communication device 913 may be a router for optical communication, a router for asymmetric digital subscriber line (ADSL), various communication modems, or the like. In one example, the communication device 913 is capable of transmitting and receiving signals and the like to and from the Internet or other communication equipment, for example, in accordance with a predetermined protocol of TCP/IP or the like. The communication device 913 may be configured as, for example, the communication unit 130 illustrated in FIG. 3, the communication unit 310 illustrated in FIG. 4, and the communication unit 410 illustrated in FIG. 5.

Moreover, the network 920 is a wired or wireless transmission path of information transmitted from a device connected to the network 920. In one example, the network 920 may include a public circuit network such as the Internet, a telephone circuit network, and a satellite communication network, various local area networks (LANs) including Ethernet (registered trademark), a wide area network (WAN), and the like. In addition, the network 920 may include a dedicated circuit network such as an interne protocol-virtual private network (IP-VPN).

The sensor 915 is various sensors such as an acceleration sensor, a gyro sensor, a geomagnetic sensor, an optical sensor, a sound sensor, a ranging sensor, and a force sensor. The sensor 915 acquires information relating to the state of the information processing device 900 itself such as the posture and moving speed of the information processing device 900, and acquires information relating to a surrounding environment of the information processing device 900 such as surrounding brightness and noise of the information processing device 900. In addition, the sensor 915 may include a GPS sensor for receiving a GPS signal and measuring the latitude, longitude, and altitude of the device. The sensor 915 may be configured as, for example, the sensor unit 110 illustrated in FIG. 3.

An example of the hardware configuration capable of implementing the functions of the information processing device 900 according to the present embodiment is illustrated above. The respective components described above may be implemented using universal members, or may be implemented by hardware that is specific to the functions of the respective components. Accordingly, it is possible to change a hardware configuration to be used appropriately depending on the technical level at each time of carrying out the embodiments.

Moreover, a computer program for implementing each of the functions of the information processing device 900 according to the present embodiment may be created, and may be mounted in a PC or the like. Furthermore, a computer-readable recording medium on which such a computer program is stored may be provided. The recording medium is, for example, a magnetic disc, an optical disc, a magneto-optical disc, a flash memory, or the like. The computer program may be distributed, for example, through a network without using the recording medium.

6. Summary

The embodiments of the present disclosure are described above in detail with reference to FIGS. 1 to 8. As described above, the sensor device 10 senses information relating to an object, and acquires attachment position information to which the attachment portion 12 is attached. The attachment portion 12 is detachably attached to one of one or more attachment positions provided on the object. The automatic acquisition of the attachment position information by the sensor device 10 makes it possible for the user to perform measurement while freely changing the attachment position of the sensor device 10, without performing troublesome input work such as setting the attachment position. In this manner, the sensor device 10 according to the present embodiment is capable of carrying out more flexibly the measurement for visualizing the action of the object.

The sensor device 10 according to the present embodiment configures settings corresponding to the characteristics of the sensor information for each attachment position by the sensor setting function. This makes it possible for the sensing system 1 to automatically acquire suitable sensor information corresponding to the attachment position of the sensor device 10. Specifically, the sensing system 1 is capable of acquiring sensor information with a suitable dynamic range and resolution by a suitable type of sensor depending on the object or the action of the object.

The sensor device 10 according to the present embodiment has the information transmission function, which allows the sensor information and the attachment position information to be transmitted to another device. In this case, it is possible for the sensor device 10 to transmit data using the compression scheme and/or the communication scheme corresponding to the attachment position. This makes it possible for the sensor device 10 to use efficiently the bandwidth in consideration of the amount of data that can vary depending on the attachment position.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In one example, the above embodiment describes that the sensor device 10 has the sensor setting function, but the present technology is not limited to this example. In one example, another device such as the smartphone 30 or the server 40 may have a sensor setting function and configure sensor setting remotely depending on the attachment position information received from the sensor device 10. The same applies to the functions of the compression scheme setting unit 145 and the communication scheme setting unit 147.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A sensor device including:

a sensor unit configured to sense information relating to an object;

an attachment portion configured to detachably attached to any of one or more attachment positions provided on the object; and an acquisition unit configured to acquire information indicating the attachment position to which the attachment portion is attached.

(2)

The sensor device according to (1), further including:

a sensor setting unit configured to configure a setting of the sensor unit.

(3)

The sensor device according to (2), in which the sensor setting unit configures the setting on the basis of the information indicating the attachment position acquired by the acquisition unit.

(4)

The sensor device according to (2) or (3), in which the sensor setting unit sets at least any of execution or stop of sensing by the sensor unit, dynamic range, and resolution.

(5)

The sensor device according to any one of (2) to (4), in which the sensor setting unit configures the setting on the basis of at least any of the object and an action performed by the object.

(6)

The sensor device according to (5), in which the sensor setting unit recognizes the action performed by the object on the basis of a user instruction.

(7)

The sensor device according to (5), in which the sensor setting unit estimates the action performed by the object on the basis of sensor information sensed by the sensor unit and the information indicating the attachment position acquired by the acquisition unit.

(8)

The sensor device according to any one of (2) to (7), further including:

a communication unit configured to transmit sensor information sensed by the sensor unit and the information indicating the attachment position acquired by the acquisition unit to another device.

(9)

The sensor device according to (8), further including:
a compression scheme setting unit configured to set a compression scheme of data to be transmitted by the communication unit depending on a content of the setting configured by the sensor setting unit.

(10)

The sensor device according to (8) or (9), further including:
a communication scheme setting unit configured to set a communication scheme to be used by the communication unit depending on a content of the setting configured by the sensor setting unit.

(11)

The sensor device according to any one of (1) to (10), in which the acquisition unit acquires the information indicating the attachment position on the basis of an electrical characteristic of the attachment position to which the attachment portion is attached.

(12)

The sensor device according to any one of (1) to (11), in which the acquisition unit acquires the information indicating the attachment position on the basis of a physical shape of the attachment position to which the attachment portion is attached.

(13)

The sensor device according to any one of (1) to (12), in which the object is a living thing.

(14)

The sensor device according to any one of (1) to (12), in which the object is a thing used by a living thing.

(15)

A sensing method that is executed by a sensor device, the sensing method including:
sensing information relating to an object; and
acquiring information indicating an attachment position to which an attachment portion is attached, the attachment portion being detachably attached to any of one or more attachment positions provided on the object.

(16)

An information processing device including:
an acquisition unit configured to acquire sensor information and information indicating an attachment position to which a sensor device is attached, the sensor information and the information indicating the attachment position being acquired by the sensor device detachably attached to any of one or more the attachment positions provided on an object; and
a processing unit configured to process the sensor information acquired by the acquisition unit on the basis of the information indicating the attachment position.

REFERENCE SIGNS LIST 1 sensing system 1
10 sensor device 10
11 main body portion
12 attachment portion
13 terminal
14 switch
110 sensor unit
120 interface unit
130 communication unit
140 control unit
141 acquisition unit
143 sensor setting unit
145 compression scheme setting unit
147 communication scheme setting unit
20 sensor mounting equipment
21 sensor fixture
22 terminal
23 concavo-convex portion
30 smartphone
310 communication unit
320 input unit
330 output unit
340 storage unit
350 control unit
351 acquisition unit
353 processing unit
355 output control unit
40 server
410 communication unit
440 storage unit
450 control unit
451 acquisition unit
453 processing unit
455 output control unit

The invention claimed is:

1. A sensor device, comprising:
a sensor configured to detect first information related to an object;
an attachment portion configured to detachably attach to at least one attachment position of a plurality of attachment positions on the object; and
a controller configured to:
acquire the first information detected by the sensor and second information, wherein the second information indicates the at least one attachment position to which the attachment portion is attached;
set, based on the second information that indicates the at least one attachment position, a compression scheme for the first information related to the object; and
control transmission of the first information related to the object based on the set compression scheme.

2. The sensor device according to claim 1, wherein the controller is further configured to set a parameter of the sensor.

3. The sensor device according to claim 2, wherein the controller is further configured to set the parameter of the sensor based on the second information indicating the at least one attachment position.

4. The sensor device according to claim 2, wherein the parameter comprises at least one of a dynamic range of the sensor or a resolution of the sensor.

5. The sensor device according to claim 4, wherein
the sensor comprises a first sensor configured to detect vibration and a second sensor configured to detect inertia, and
the controller is further configured to:
turn ON the first sensor to detect the first information and set a wide dynamic range of the second sensor based on a first attachment position of the plurality of attachment positions on the object; and
turn OFF the first sensor and set a narrow dynamic range of the second sensor based on a second attachment position of the plurality of attachment positions on the object.

6. The sensor device according to claim 2, wherein the controller is further configured to set the parameter of the sensor based on at least one of the object or an action executed by the object.

7. The sensor device according to claim 6, wherein the controller is further configured to recognize the action executed by the object based on a user instruction.

8. The sensor device according to claim 6, wherein the controller is further configured to estimate the action executed by the object based on the first information and the second information.

9. The sensor device according to claim 2, wherein the controller is further configured to transmit the first information and the second information to an external device.

10. The sensor device according to claim 9, wherein
the controller is further configured to set the compression scheme based on an amount of the first information, and
the amount of the first information is based on the at least one attachment position.

11. The sensor device according to claim 9, wherein the controller is further configured to set a communication scheme based on an amount of the first information.

12. The sensor device according to claim 1, wherein the controller is further configured to acquire the second information indicating the at least one attachment position based on an electrical characteristic of the at least one attachment position to which the attachment portion is attached.

13. The sensor device according to claim 1,
further comprising a switch, wherein
the at least one attachment position has a physical shape of a determined pattern to sequentially press the switch, and
the controller is further configured to acquire the second information indicating the at least one attachment position based on an alignment of the determined pattern of the at least one attachment position and the switch.

14. The sensor device according to claim 1, wherein the object is a living thing.

15. The sensor device according to claim 1, wherein the object is a tool used by a living thing.

16. The sensor device according to claim 1, wherein
the second information comprises identification information of the at least one attachment position, and
the identification information of the at least one attachment position specifies a specific position on the object.

17. A sensing method, comprising:
in a sensor device that comprises an attachment portion:
detecting first information related to an object, wherein the attachment portion is configured to detachably attach to at least one attachment position of a plurality of attachment positions of the object;
acquiring the first information and second information, wherein the second information indicates the at least one attachment position to which the attachment portion is attached;
setting, based on the second information that indicates the at least one attachment position, a compression scheme for the first information related to the object; and
controlling transmission of the first information related to the object based on the set compression scheme.

18. An information processing device, comprising:
a controller configured to:
acquire first information related to an object from a sensor device based on a compression scheme;
acquire second information indicating at least one attachment position to which the sensor device is attached, wherein
the sensor device is detachably attached to the at least one attachment position of a plurality of attachment positions on the object, and
the compression scheme is set based on the second information indicating the at least one attachment position;
process the first information based on the second information; and
determine a posture of the object based on the processed first information.

19. A sensor device, comprising:
a sensor configured to detect first information related to an object;
a switch;
an attachment portion configured to detachably attach to at least one attachment position of a plurality of attachment positions on the object, wherein the at least one attachment position has a physical shape of a determined pattern to sequentially press the switch; and
a controller configured to:
acquire the first information detected by the sensor;
acquire second information that indicates the at least one attachment position to which the attachment portion is attached, wherein the second information is acquired based on an alignment of the determined pattern of the at least one attachment position and the switch; and
control transmission of information of a posture of the object based on the first information and the second information.

* * * * *